(12) United States Patent
Chow et al.

(10) Patent No.: US 9,974,311 B2
(45) Date of Patent: May 22, 2018

(54) IMPREGNATED ODOUR CONTROL PRODUCTS AND METHODS OF MAKING THE SAME

(71) Applicant: LIFE SCIENCE TGO, S.R.L., Bridgetown (BB)

(72) Inventors: Philip P. Chow, Markham (CA); Catherine Ciupa, Toronto (CA)

(73) Assignee: STEWART GROUP TRADING INC., Ontario (CA)

(*) Notice: Subject to any disclaimer, the term of this patent is extended or adjusted under 35 U.S.C. 154(b) by 116 days.

(21) Appl. No.: 14/034,109

(22) Filed: Sep. 23, 2013

(65) Prior Publication Data

US 2015/0086519 A1    Mar. 26, 2015

(51) Int. Cl.
| | |
|---|---|
| *A01N 63/00* | (2006.01) |
| *B29C 45/00* | (2006.01) |
| *B29C 43/00* | (2006.01) |
| *B29D 7/01* | (2006.01) |
| *B29C 47/00* | (2006.01) |
| *B29D 35/00* | (2010.01) |
| *B29D 35/12* | (2010.01) |
| *B29C 49/00* | (2006.01) |
| *A43B 1/00* | (2006.01) |
| *A43B 13/04* | (2006.01) |
| *B29B 7/34* | (2006.01) |
| *B29K 101/12* | (2006.01) |
| *B29K 511/00* | (2006.01) |
| *B29K 105/00* | (2006.01) |
| *B29K 23/00* | (2006.01) |
| *B29K 105/04* | (2006.01) |

(52) U.S. Cl.
CPC ............ *A01N 63/00* (2013.01); *A43B 1/0045* (2013.01); *A43B 13/04* (2013.01); *B29B 7/34* (2013.01); *B29C 43/003* (2013.01); *B29C 45/0001* (2013.01); *B29C 47/00* (2013.01); *B29C 47/0004* (2013.01); *B29C 49/00* (2013.01); *B29D 7/01* (2013.01); *B29D 35/0009* (2013.01); *B29D 35/122* (2013.01); *B29C 49/0005* (2013.01); *B29C 2049/001* (2013.01); *B29K 2023/083* (2013.01); *B29K 2101/12* (2013.01); *B29K 2105/0029* (2013.01); *B29K 2105/0041* (2013.01); *B29K 2105/04* (2013.01); *B29K 2511/00* (2013.01)

(58) Field of Classification Search
CPC ........ A01N 63/00; A43B 1/0045; A43B 13/04
See application file for complete search history.

(56) References Cited

U.S. PATENT DOCUMENTS

| | | | |
|---|---|---|---|
| 3,767,790 A | 10/1973 | Guttag | |
| 4,634,672 A | 1/1987 | Baumgarten et al. | |
| 4,722,898 A | 2/1988 | Errede et al. | |
| 5,132,211 A | 7/1992 | Lundin et al. | |
| 5,284,587 A | 2/1994 | Wong et al. | |
| 6,670,407 B2 | 12/2003 | Howdle et al. | |
| 6,716,435 B1 * | 4/2004 | Farmer et al. | 424/400 |
| 6,967,025 B2 * | 11/2005 | Di Cintio et al. | 424/402 |
| 7,820,420 B2 * | 10/2010 | Whitlock | 435/170 |
| 2003/0165472 A1 | 9/2003 | McGrath et al. | |
| 2005/0084532 A1 | 4/2005 | Howdle et al. | |

FOREIGN PATENT DOCUMENTS

| | | |
|---|---|---|
| CN | 102180617 | 9/2011 |
| CN | 102389708 | 3/2012 |
| CN | 102389708 * | 3/2013 |
| CN | 102180617 * | 9/2014 |
| EP | 0 732 396 | 9/1996 |
| WO | 98/47374 | 10/1998 |
| WO | 01/52913 | 7/2001 |

* cited by examiner

*Primary Examiner* — Vera Afremova
(74) *Attorney, Agent, or Firm* — Fitzpatrick Cella Harper and Scinto

(57) ABSTRACT

A product capable of controlling odors arising from organic matter, and a method of making the product. The product comprises an admixture of a moldable thermoplastic and a benign dormant bacteria in a sporulated form, which admixture is formed by mixing the benign dormant bacteria into the moldable thermoplastic when the moldable thermoplastic is melted, and molding the admixture into a molded product. The benign dormant bacteria are embedded throughout the molded product, including being buried within a body of the molded product and being presented on a surface of the molded product. The benign dormant bacteria presented on the surface of the molded product are activatable upon exposure of the surface of the molded product to the organic matter, and the benign activated bacteria digest the organic matter to control production of offensive odors. Abrasive wear of the surface of the molded product exposes fresh benign dormant bacteria buried in the body to the surface for additional odor control.

38 Claims, 5 Drawing Sheets

IMPREGNATED ODOUR CONTROL PRODUCTS AND METHODS OF MAKING THE SAME

BACKGROUND OF THE INVENTION

1. Field of the Invention

Figure 1:
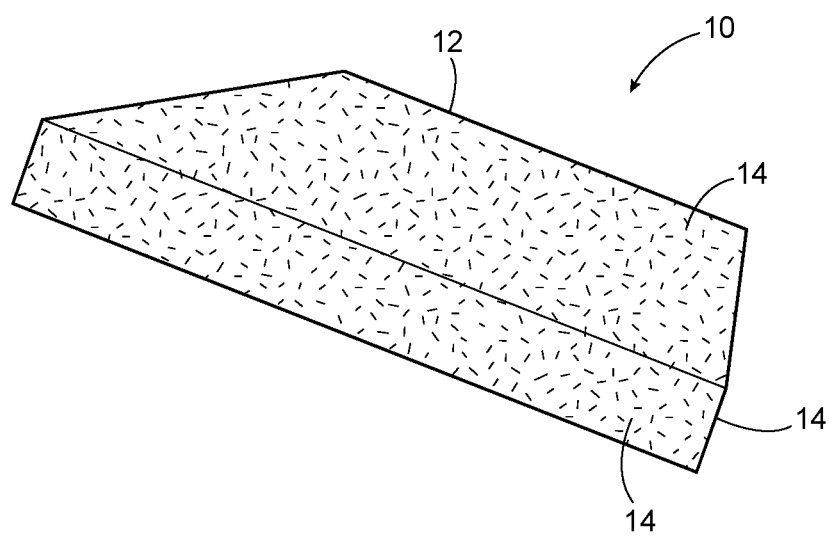

Materials which are capable of controlling odour arising from certain organic matter. More particularly, materials are configured to control odours by using benign bacterial agents to consume and digest the organic matter which can otherwise lead to bad odours and to a method of manufacturing such odour control materials. The effect of the odour control materials is long lasting.

2. Description of the Prior Art

There are many instances where owing to deposits of organic matter on surfaces, offensive odours can arise through the presence of the organic matter and its decomposition. In fact, many materials utilized in household applications are susceptible to soiling by organic based material, which if allowed to remain, can give rise to malodours.

Deposits of organic materials on surfaces may also give rise to other concerns. Many of the organic materials, such as bodily fluids like sweat, blood and saliva, organic waste such as feces and urine, spilt food such as syrup and eggs, and beverages such as milk, wine and soft drinks etc., are capable of supporting bacterial growth. Some of the bacteria that may grow as a result of a deposit of organic material may give rise to odour due to decomposition and incomplete digestion of the organic material. Some of the bacteria may also have the potential of causing disease in persons exposed to them.

In order to control/reduce odours, there have been attempts to reduce the number of bacteria present on surfaces by utilizing various anti-microbial agents. See for example U.S. Pat. Nos. 4,110,504 and 5,024,840, which describe applying anti-microbial agents to carpet in a manner similar to the way stain blockers are applied to carpet. However, the use of anti-microbials raises concerns such as the potential that some of the bacteria may become resistant to effects of the anti-microbials, and the release of such anti-microbials into the environment may have a detrimental effect on the environment.

Many bacterial and fungal genera are known for use in odour control due to their capability for producing enzymes that are capable of breaking down organic material. Several such bacterial genera such as *Bacillus, Lactobacillus, Enterobacter, Streptococcus, Nitrosomonas, Nitrobacter, Pseudomonas, Alcaligens* and *Klebsiella* amongst others are known for use in such applications, with *Bacillus* and *Lactobacillus* sp. being the most prevalent in use in various applications.

For example, European Patent Application No. 732,396 describes use of *Bacillus* sp. for odour control of feedstuffs used in farming and JP Patent Application No. 7-031,668 describes its use for odour control of toilets, shoe boxes and pet litter. Other uses of *Bacillus* for odour control baby diapers and wallpaper are described in JP Patent Application Nos. 2-2-121,665 and 3-059,199 respectively. Preparations of sporulated *Bacillus* in a form suitable for spraying or otherwise distributing on a deposit, especially of pet urine and feces, on a carpet for controlling odour are presently marketed by The Bramton Company of Dallas, Tex. under the trademark OUTRIGHT. Once the deposit is deodorized, the bacteria are depleted from the site or disposed of along with the deodorized material. In the event of a new deposit of organic material on the carpet, the treatment must be repeated.

U.S. Pat. Nos. 6,974,691 and 7,314,748 disclose methods for controlling odour associated with spills of organic material which involve applying to surfaces, including carpet, plastic and wood, a preparation of dormant bacteria, which when activated are effective to control odours. The dormant bacterial preparation is adhered to the surface, such that when the treated surface is exposed to organic material which can cause odours, the dormant bacteria are capable of becoming active and digest the organic material.

Although, the methods described in the U.S. '691 and '748 patents are effective for surface treating fibrous materials, including carpet, batting used for mattresses, pillows and pads, as well as other relatively porous surfaces encountered in the household or commercial environment, semi-porous surfaces such as wood and nonporous surfaces such as plastic, they are not effective in treating non-fibrous materials that are subjected to surface abrasion. Therefore, there remains a need to counteract the effects of deposits of organic material, and especially for controlling odour associated with the deposits, including in non-fibrous materials such as thermoplastics, where the effects of the odour control are preventative and long lasting, even in high wear applications.

Other patent documents of general interest include: Canadian Pat. Document Nos. 2,243,011 and 2,369,469; U.S. Pat. Nos. 3,636,927, 3,720,606, 3,720,606, 3,892,846, 3,941,090, 4,465,019, 4,607,594, 4,680,212, 4,704,989, 4,839,212, 4,844,010, 4,925,707, 4,946,672, 5,154,594, 5,683,575, 5,741,553, 5,863,882, 6,265,191, 6,325,934, 6,967,025, 7,507,402, 7,795,119; U.S. Pat. App. Pub. Nos. 2003/0003138, 2003/0012810, 2003/0089381, 2003/0126688, 2008/0075794 and 2012/0114579; PCT Intl Pat. App. Pub. Nos. 96/19611, 97/25865, 99/46350, 00/03752, 00/63338, 02/33035, 03/056096, 03/064755; Pat. App. Pub. Nos. 0039522, 0076447, 0476915, 0878202, and 1096959; U.K. Pat. App. Pub. No. 2362814; Japanese Pat. Document Nos. 5-153971, 7-222790, and 9-28377; Czechoslovakian Pat. Document No. CS246119; and Soviet Union Pat. Document No. SU1091889.

Figure 5:
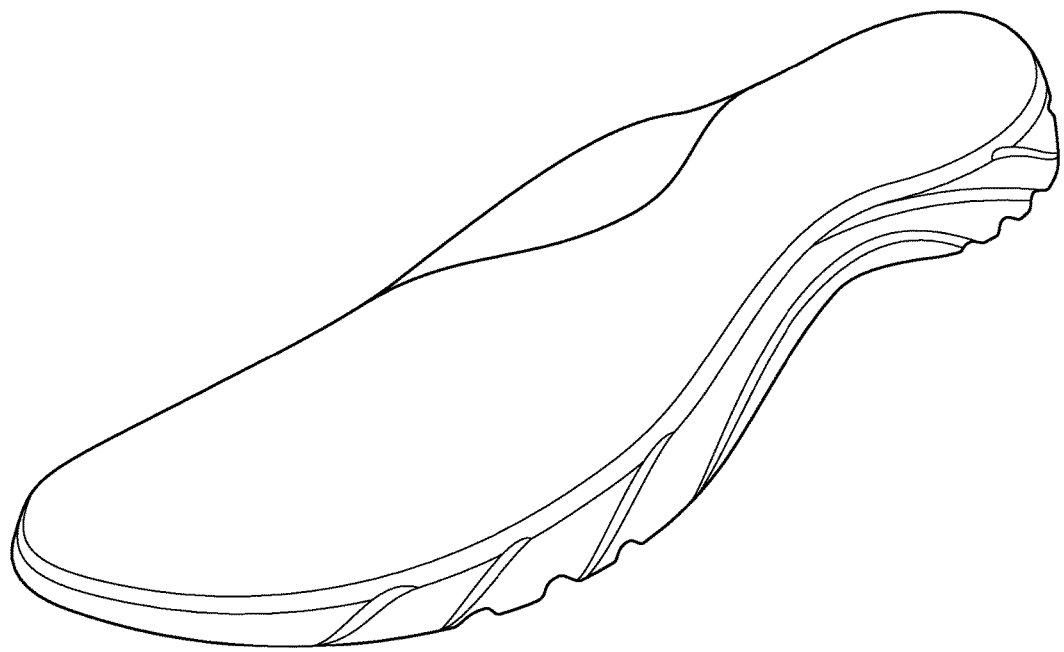
Figure 6:
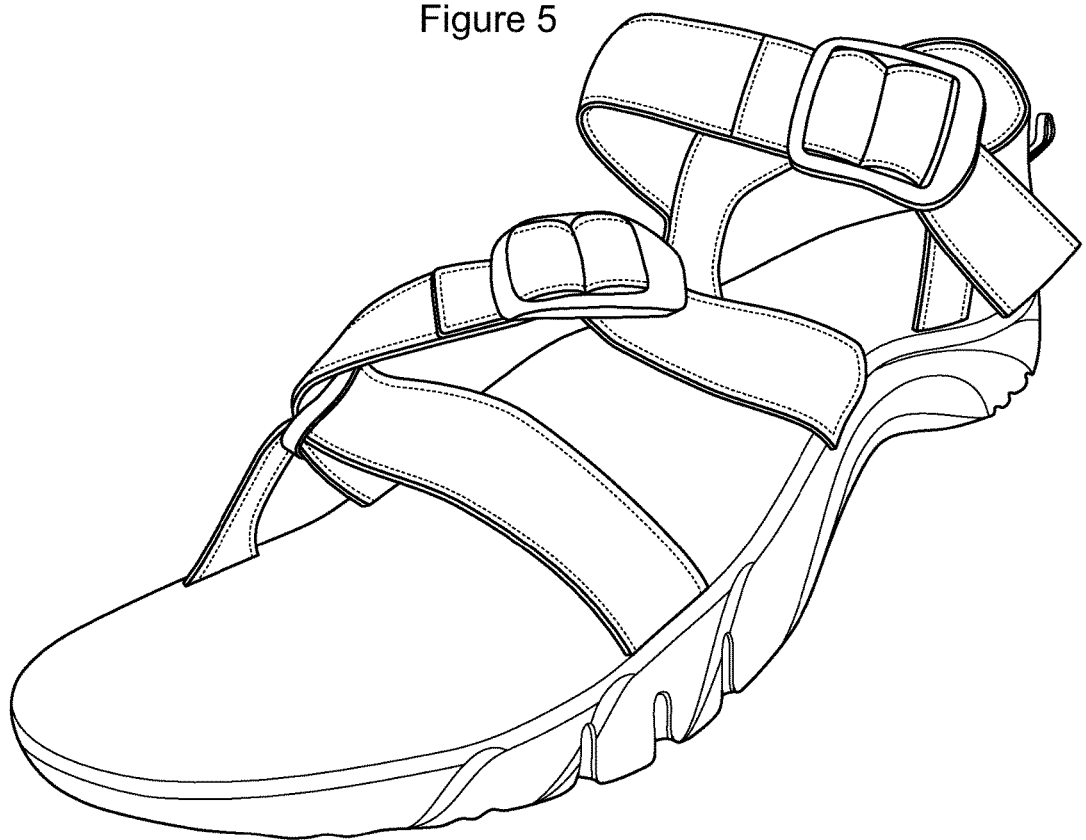
Figure 7:
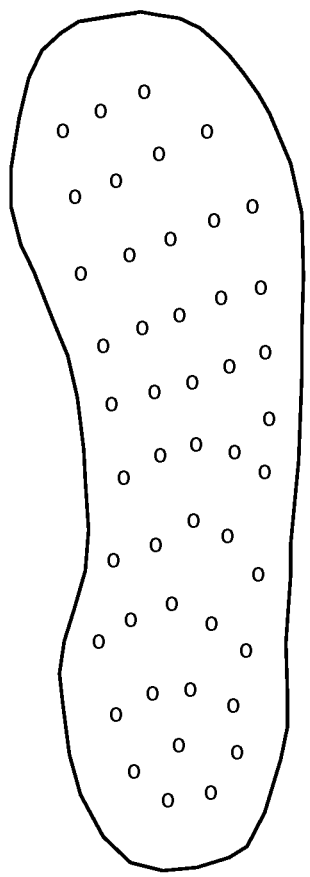

Other non-patent documents of general interest include:
Brochure for BI-CHEM® BIOCLEAN Carpet Cleaner;
Brochure for BI-CHEM® GC 600L;
Brochure for BI-CHEM® MSB 4X;
Chemical Abstracts, vol. 108, No. 19, May 1998, Abstract No. 169120y; XP002122802;
CHEMICAL ABSTRACTS, vol. 108, no. 20, May 1998 (1998-05) Columbus, Ohio, US; abstract no. 169120y, XP002122802 & CS 246 119 A (DOSTAL JAROSLAV; WEST MIROSLAV) 16 Oct. 1986 (1986-10-16);
DATABASE WPI Section Ch, Week 199715 Derwent Publications Ltd., London, GB; Class A97, AN 1997-159089 XP002122803 & JP 09 028377 A (AZUMA K), 4 Feb. 1997 (1997-02-04);
Database WPI, Week 199329, Derwent Publications Ltd., London, GB; An 1993-231489; XP002210738 Deodorise Supress Excretion Bad Smell Contain *Bacillus* Magaterium Effect Range Malodorous Smell;
Hans G. Schegel et al., General Microbiology, 7.sup.th ed., p. 83 (1993);
Response to Summons in Opposition by Novozymes Biologicals, Inc. in European Patent No. 1 096 959 B1 with attached Declaration and Exhibits (139 pages) (August 2005); and XP002210738 Deodorise Supress Excretion Bad Smell Contain *Bacillus megaterium* Effect Range Malodorous Smell.

SUMMARY OF THE INVENTION

An object is to provide an improved product capable of controlling odours arising from organic matter, and methods of making the product.

This object and others are provided by a molded (i.e. compression molded, injection molded, blow molded, extrusion molded, etc.) Ethylene Vinyl Acetate (EVA) thermoplastic, having benign dormant bacteria embedded generally throughout, buried within, and presented on the surface thereof. The benign dormant bacteria presented on the surface of the molded product are activatable, upon exposure to organic matter, to generate enzymes and digest the organic matter while controlling the production of offensive odours. Abrasive wear of the surface of the molded product exposes fresh benign dormant bacteria buried within the molded product to the surface of the product to provide renewed and additional odour control.

Examples of molded products include automotive products such as car seats, child safety seats, carpet underlay, and headliners; marine products such as life jackets; electronics accessory products such as work station mats and mouse pads; sport and leisure products such as sports mats, gym mats exercise mats, yoga mats, garden mats, personal protective equipment, sport protective pads, toys and games, camping bedrolls, backpacks, hand shopping baskets, luggage, travel bags and visors; footwear such as shoes, clogs, flip flops, slippers, insoles and boots; and toys such as play mats and blocks, etc.

According to an embodiment the molded product is formed into fibers, pellets, sheets, blocks or tiles.

According to another embodiment the sheet, block, or tile form of the molded product is formed into a secondary structure by cutting, abrading, shaping, forming or additional molding.

According to another embodiment the fiber form of the molded product is formed into a secondary structure by braiding, twisting, weaving, knitting, crocheting, knotting, spinning, crimping or felting.

According to yet another embodiment of the present invention the secondary structure is formed into threads, yarns or textiles.

Examples of textiles include floor coverings, bedding, drapery, upholstery, a towel, at least a portion of an article of clothing, and at least a portion of a footwear.

Examples of floor coverings include carpets, carpet tiles, mats and rugs.

Examples of articles of clothing include dresses, coats, socks, pants, shirts, jackets and headwear.

Therefore, in accordance with one embodiment there is provided a product capable of controlling odours arising from organic matter, said product comprising:

an admixture of a moldable thermoplastic and benign dormant bacteria in a sporulated form, formed by admixing said benign dormant bacteria into said moldable thermoplastic when said moldable thermoplastic is melted, said admixture being molded into a molded product;

said benign dormant bacteria being embedded throughout said molded product, including being buried within a body of said molded product, including being presented on a surface of said molded product, said benign dormant bacteria presented on said surface being activatable upon exposure of said surface to said organic matter;

wherein said benign activated bacteria digest said organic matter to control production of offensive odours, and abrasive wear of said surface of said molded product exposes fresh benign dormant bacteria buried within said body to said surface for additional odour control.

In accordance with another aspect there is provided a secondary structure formed by cutting, abrading, shaping, forming, or additional molding, a sheet, block or tile form of the above product.

In accordance with another aspect there is provided a secondary structure formed by braiding, twisting, weaving, knitting, crocheting, knotting, spinning, crimping or felting a fiber form of the above product.

In accordance with yet another aspect of the present invention, there is provided a method of making a product capable of controlling odours arising from organic matter, comprising the steps of:

a) melt-blending at a bacteria compatible temperature range:
   i) a moldable thermoplastic; and
   ii) benign dormant bacteria in a sporulated form; and
b) forming the melt-blended product of step (a) into a molded product, with said benign dormant bacteria being embedded throughout said molded product, including being buried within a body of said molded product and being presented on a surface of said molded product, said benign dormant bacteria presented on said surface being activatable upon exposure of said surface to said organic matter;

wherein said benign activated bacteria digest said organic matter to control production of offensive odours and abrasive wear of said surface of said molded product exposes fresh benign dormant bacteria buried within said body to said surface for additional odour control.

In accordance with yet another aspect there is provided a product capable of controlling odours arising from organic matter, said product being formed by the above method.

In accordance with yet another aspect there is provided a use of benign dormant bacteria in a sporulated form in the preparation of a product capable of controlling odours arising from organic matter, said product comprising an admixture of a moldable thermoplastic and benign dormant bacteria in a sporulated form, formed by admixing said bacteria and said moldable thermoplastic when said moldable thermoplastic is melted, said admixture being molded into a molded product, said benign dormant being embedded throughout said molded product, including being buried within a body of said molded product and being presented on a surface of said molded product, said benign dormant bacteria presented on said surface being activatable upon exposure of said surface to said organic matter, wherein said benign activated bacteria digest said organic matter to control production of offensive odours and abrasive wear of said surface exposes fresh benign dormant bacteria buried within said body to said surface for additional odour control.

BRIEF DESCRIPTION OF THE DRAWINGS

FIG. 1 is a product according to one embodiment;

FIG. 2 are results of tests of bacterial growth in test specimens of the product of FIG. 1;

FIG. 3 is a footbed for a sandal according to another embodiment of the present invention;

FIG. 4 is a sandal assembled using the footbed of FIG. 3;

FIG. 5 is a footbed for a sandal according to another embodiment of the present invention;

FIG. 6 is a sandal assembled using the footbed of FIG. 5; and FIG. 7 is an insole for a shoe according to another embodiment of the present invention.

DETAILED DESCRIPTION OF THE PREFERRED EMBODIMENTS

The present invention is described in more detail with reference to exemplary embodiments thereof as shown in the appended drawings. While the present invention is described below including preferred embodiments, it should be understood that the present invention is not limited thereto. Those of ordinary skill in the art having access to the teachings herein will recognize additional implementations, modifications, and embodiments which are within the scope of the present invention as disclosed and claimed herein.

A product capable of controlling odours arising from organic matter is shown generally with reference numeral 10 in FIG. 1. Product 10 is an admixed combination of a moldable thermoplastic containing benign dormant bacteria 12 in a sporulated form, which combination was melt-blended and molded into a molded product, in this case a sheet, from which the square piece of product 10, shown in FIG. 1, was cut. Preferably, the moldable thermoplastic is an ethylene vinyl acetate (EVA), however, as discussed in more detail below, different suitable moldable thermoplastics may be utilized as desired. The benign dormant bacteria 12 are embedded generally throughout the product 10, including being buried within the body of the product 10 as well as being presented on the surface 14 of the product 10. The benign dormant bacteria 12 presented on the surface 14 of the product 10 are activatable upon exposure of the surface 14 of the product 10 to organic matter. When activated, bacteria 12 digest the organic matter to control production of offensive odours.

Preferably, the product 10 contains a surface population of the dormant bacteria 12 large enough to digest the organic matter at a rate sufficient to control by reducing or eliminating odours associated with the organic matter. In this regard, good results have been obtained with between $10^6$ and $10^8$ of the benign dormant bacteria 12, estimated by calculating colony forming units (cfu), being present on the surface of the product 10, per square inch. Preferably, the surface population of the benign dormant bacteria 12 will be at least $10^7$ cfu per square inch.

Beneficially, abrasive wear of the surface 14 of the product 10 exposes fresh benign dormant bacteria buried in the body to the surface 14 for additional odour control. Accordingly, the product 10 contains a buried population of the benign dormant bacteria 12 large enough to continue to digest the organic matter at a rate sufficient to control odours associated with the organic matter as the surface wears. In this regard, good results have been obtained with between $10^{12}$ and $10^{16}$ of the benign dormant bacteria 12 being present per cubic inch of the product 10.

The present invention comprehends adding an effective amount of benign dormant bacteria to reduce and thus control odours. While certain ranges are identified it will be understood that different applications may have different insult levels typically, which can vary. For example, a shoe insole may have a heavy daily load of sweat, whereas another application may not receive such continual insults. In all cases it is preferable to provide the beneficial bacteria are present on a surface initially when insults occur, and to remain present during and after wear due to being incorporated into the material. As such the specific amounts of bacteria present are intended to be shown as examples and not as limitations per The product 10 is preferably made by first melt-blending at a bacteria compatible temperature range a mixture comprising a moldable thermoplastic, then continuing to blend the moldable thermoplastic mixture in a double-roller blending or kneading machine, and adding a mixture of benign dormant bacteria in a sporulated form. Preferably, one or more of a foaming agent (i.e. 3 to 10% w/w), a cross-linking agent (i.e. 1 to 5% w/w), a lubricant (i.e. 0.5% to 2% w/w), and a filler, can be included in the moldable thermoplastic mixture depending on the application, as will be appreciated by persons skilled in the art. The ingredients may be melt-blended together all at once, or in separate stages. In generally, it has been found that up to 1% w/w of an aqueous mixture of benign dormant bacteria can be added to a moldable thermoplastic mixture comprising EVA. However, it is contemplated that lower or higher % w/w of aqueous mixture of benign dormant bacteria may be used, depending on the moldable thermoplastic being used, for example in the range of 0.01% to 5%

The bacteria compatible temperature range is governed mostly by the melting temperature of the moldable thermoplastic being used, and temperatures of up to 175° C. have yielded acceptable results. It is helpful that the bacteria compatible temperature range be sufficient to melt the moldable thermoplastic so that the mixture of benign dormant bacteria and other ingredients will homogeneously blend or knead, and an effective amount of the benign dormant bacteria will be present to control odours. It will be understood that the bacteria compatible temperature range does not exceed a temperature at which the sporulated bacteria are destroyed. While certain bacteria compatible temperature ranges are identified it will be understood that different applications will require different temperatures. As such the temperatures described herein are intended to be shown as examples only and not as limitations.

The melt-blended product is then transferred from the blending/kneading machine and formed by molding into the molded with the benign dormant bacteria 12 being embedded generally throughout the product 10, including being buried within the body of the product 10 and being presented on a surface 14 of the product 10. The benign dormant bacteria 12 presented on the surface 14 of the product 10 are activatable upon exposure of the surface 14 of the product 10 to the organic matter, upon activation, the benign activated bacteria digest the organic matter to control production of offensive odours. As mentioned above, abrasive wear of the surface 14 of the product 10 preferably exposes fresh benign bacteria 12 buried in the body to the surface 14 for additional odour control.

The moldable thermoplastic may be an open-cell foam, or a close-cell foam, which can be compression molded, injection molded, blow molded, or extrusion molded, according to techniques well known in the art. Although preferred thermoplastics are EVA, those persons skilled in the art will appreciate that other moldable thermoplastic materials may be used in place of EVA, such as for example a polyethylene, a polypropylene, a polyvinyl chloride, a polyamide, an elastane or a polystyrene. All such moldable thermoplastics may be used herein.

It is important that the moldable thermoplastic mixture, when combined with the mixture of benign dormant bacteria, can be molded into the specific shape desired for the product 10, and a sufficient amount of the benign dormant bacteria 14 survive the processing and molding steps to form the product 10. The product 10 may be formed into numerous shapes and sizes for countless applications.

For example, the product 10 may be formed into a fiber by extruding the moldable thermoplastic mixture impregnated with the mixture of benign dormant bacteria into fibers or filaments. The present invention also contemplates forming a secondary structure by braiding, twisting, weaving, knitting, crocheting, knotting, spinning, crimping, or felting, the fiber form of product 10, using techniques which are well known in the art.

Alternately, the product 10 may be formed into a sheet, a block, or a tile, by compression molding, injection molding, blow molding, or extrusion molding, using techniques well known in the art.

For example, compression molding can be used to make insoles for shoes, as follows. After forming the melt-blended product containing the moldable thermoplastic mixture and the mixture of benign dormant bacteria, it is kneaded at room temperature (i.e. about 20 to 25° C.) for about 10 minutes, and then rolled into sheets. The sheets are cut, compressed into large sheets at 170° C. to 175° C., and a pressure of about 150 kg/cm$^2$ for 10 to 20 minutesduring which process cross-linking takes place and the product is foamed. It is then pressed into an insole mold at approximately 160° C. for 15 minutes.

As another example, injection molding can be used to make one piece shoes, as follows. After forming the melt-blended product containing the moldable thermoplastic mixture and the mixture of benign dormant bacteria, it is brought to a temperature of 70° C. and injected into a mold. The mold is then hot pressed in an oven at 160° C. for 7 minutes.

Forming a secondary structure by cutting, abrading, shaping, forming, or additional molding, the sheet, block, or tile, using well known techniques, is also contemplated.

As can now be appreciated, the moldable thermoplastic mixture impregnated with the benign dormant bacteria, can be made in large batches, and formed into bricks that are then cut into sheets, or it can be extruded into sheets, in either case, the sheets can then be put into molds and cold or hot formed into shapes, such as, for example, insoles or sandal beds. Alternately, the moldable thermoplastic mixture impregnated with the benign dormant bacteria can be extruded, placed onto molds, or injected into molds, for shaping.

The following is a non-exhaustive list of the numerous applications contemplated for the product 10 according to various embodiments of the present invention:
threads;
yarns;
textiles;
floor coverings (i.e. carpets; carpet underlays; carpet tiles; mats including sports mats, gym mats, exercise mats, yoga mats, children's play mats, and garden mats; and rugs);
bedding;
drapery;
upholstery;
towels;
articles of clothing or portions thereof (i.e. dresses, coats, socks, pants, shirts, headwear, and jackets);
footwear or portions thereof (i.e. sandals, shoes, boots, slippers, flip flops, clogs, insoles, footbeds, and outsoles);
body protective gear
toys and games (i.e. play mats, blocks);
automotive products (i.e. car seats, child safety seats, carpet underlay, and headliners);
marine products (i.e. life jackets);
electronics accessory products (i.e. work station mats, mouse pads);
sport and leisure products (i.e. sports mats, gym mats, exercise mats, yoga mats, garden mats, personal protective equipment, sport protective pads, camping bedrolls, backpacks, hand shopping baskets, luggage and travel bags, and visors).

Many bacterial genera are known to produce enzymes that are capable of breaking down organic matter. Such bacteria are particularly useful where the organic matter, if allowed to remain, will give rise to malodours. Several such bacterial genera such as *Bacillus, Lactobacillus, Enterobacter, Streptococcus, Nitrosomonas, Nitrobacter, Pseudomonas, Alcaligens*, and *Klebsiella* amongst others are known for use in such applications, with *Bacillus* and *Lactobacillus* sp. being the most prevalent in use in various applications. Strains of bacteria from the genera *Bacillus* are useful in practicing the present invention. The preferred benign dormant bacteria 12 are those which when activated by the presence of organic matter, produce an enzyme to break down and assist with digesting the organic matter, creating only water and carbon dioxide as by-products. Once the organic matter has been digested the preferred benign dormant bacteria 12 return to a dormant state until organic matter is presented again and the cycle repeats.

Preferably, the mixture of benign dormant bacteria for use in the present invention includes one or more strains of *Bacillus megaterium, Bacillus subtilus, Bacillus Licheniformis, Bacillus Cerus, Bacillus, Alvei, Bacillus Coagulans, Bacillus Pumillus, Bacillus Simplex, Bacillus Brevis*, and *Bacillus Amyloliquefaciens*, which are available for example from Envera, LLC, whose address is 220 Garfield Ave., West Chester, Pa., 19380, U.S.A. More preferably, the strains of bacteria for use in the present invention are selected from *Bacillus megaterium, Bacillus subtilus*, and *Bacillus Licheniformis* species. Each of these species a) effectively express enzymes that break down particular types of organic matter, without producing odorous metabolites, b) are ubiquitous in nature, c) are non-hazardous to humans, and d) are included in the Domestic Substances List (DSL) in Canada, and are therefore eligible to be imported and used within Canada.

The selection of the strains of bacteria for use in the present may depend upon many factors. One such factor is the nature of the organic matter most commonly expected for the particular application. However, the most common forms of organic matter include bodily fluids, or organic waste. In most cases, to activate the benign dormant bacteria, the organic matter will need to contain carbon, nitrogen, and sufficient moisture content. Typically the bodily fluids include sweat, blood, saliva, and semen. Typical organic wastes include feces, urine, soil, beverages, such as, tea, milk, wine, and soft drinks, other food, such as, syrup, and eggs, and like.

In an indoor environment, the nature of the deposits of organic matter may differ from those of an outdoor environment. Therefore, due consideration may need to be given to the environment where the product 10 will most likely be used. Depending upon the nature of the deposited organic matter, the mixture of benign dormant bacteria 12 may be selected to contain strains having enhanced activity against such materials. Another factor that may affect the nature of the deposit is the geographical location of the surface of the product. This factor would especially relate to the nature of deposits of out-doors soil and to the nature of food deposits. Different regions are known to have different soil types and different regions may also have differences in the foods commonly consumed due to cultural and environmental factors. In addition, the temperature of the product will influence the activity of the bacteria. Depending on the strain selected the bacteria will tend to exhibit enhanced activity at higher temperatures. At lower ambient temperatures, more active strains may be desired.

The mixture of benign dormant bacteria will typically comprise of one or more strains selected from the species described above, and a carrier. When utilizing a mixture of more than one strain, each of the individual strains may comprise between 3% and 97% of the total of the benign dormant bacteria present in the mixture. These percentages are based on the total cell number. When mixtures of more than two strains are employed, each of the strains is most preferably present in an amount of from 10% to 60% of the total bacteria in the preparation. Particularly preferred mixtures of benign dormant bacteria for general use in almost all applications are as follows:

| Species | % of Total Bacteria | | |
|---|---|---|---|
| | Range | Preferred Range | Most Preferred |
| Bacillus megaterium | 3-97 | 5-15 | 10 |
| Bacillus subtilus | 3-97 | 10-50 | 30 |
| Bacillus licheniformis | 3-97 | 40-80 | 60 |

* Total benign dormant bacteria in mixture equals 100%

In a preferred embodiment of the present invention an effective amount of a bacterial composition comprising one or more strains selected from the group consisting of *Bacillus megaterium, Bacillus subtilus, Bacillus Licheniformis, Bacillus Cerus, Bacillus, Alvei, Bacillus Coagulans, Bacillus Pumillus, Bacillus Simplex, Bacillus Brevis*, and *Bacillus Amyloliquefaciens* are provided in a state in which the composition may be combined with a moldable thermoplastic material. The effective amount is a sufficient number of benign dormant bacteria 12 to provide a relatively uniform coverage on the surface 14 of the product 10 such that when any portion of the surface 14 is exposed to a deposit of an odour causing organic matter, the activated benign bacteria will undergo rapid growth and consume the odour causing organic matter. The factors that can affect the number of benign dormant bacteria 12 to be used relate in most part to the nature of the product 10. As mentioned above, however, for most products between about $10^6$ and $10^8$ benign dormant bacteria per square inch of the surface 14 of the product is most effective with about $10^7$ cfu per square inch being most preferred.

The bacteria may be provided in an aqueous carrier or a dry powder carrier. The purpose of the carrier is to transport the benign dormant bacteria 12 to, and facilitate with dispersing the benign dormant bacteria 12 throughout, the melt-blended mixture of moldable thermoplastic during the kneading step. In this regard, the aqueous carrier is preferred over the dry powder carrier, because the dry powder carrier has been found to be susceptible to dispersing into the air when being applied to the kneading moldable thermoplastic mixture. This phenomenon is problematic because when portions of the benign dormant bacteria mixture are dispersed into the air, concentrations of some components of the melt-blended product will vary, which may adversely affect characteristics of the resulting product 10.

Distilled water can be used as the aqueous carrier if the benign dormant bacteria mixture will be combined with the moldable thermoplastic mixture immediately. According to this embodiment, the benign dormant bacteria 12 are in a spray dried, dry powder form, and simply rehydrated in the water to form the benign dormant bacteria mixture on site, just before the benign dormant bacteria mixture is combined with the moldable thermoplastic mixture, as discussed above. Preferably, the aqueous benign dormant bacteria mixture contains between 0.0001% and 2% w/w of the benign dormant bacteria, with the remainder being distilled water. What is desired is for the aqueous benign dormant bacteria mixture to contain a sufficient amount of benign dormant bacteria to result in at least $10^6$ benign dormant bacteria being present at the surface of the product 10 per square inch, as mentioned above, without introducing too much water to the moldable thermoplastic mixture so as not to significantly alter the characteristics or quality of the resulting product.

However, if the benign dormant bacteria mixture will not be used immediately, the aqueous form of the benign dormant bacteria mixture will preferably also include:

0.1% to 10% w/w of a surfactant, such as sodium lauryl sulphate, glucopon, or sterol, to break up the benign dormant bacteria clumps and disperse them in the solution;

0.03% to 2% of a buffer, such as a phosphate based buffer system comprising a blend of potassium phosphate monobasic and potassium phosphate dibasic, to maintain a pH of 6.5 to 7.5; and 0.001% to 1% preservative, such as a biocide, to a) prevent the benign dormant bacteria from germinating, and b) prevent contamination of the benign dormant bacteria mixture with outside bacteria.

It is contemplated that the benign dormant bacteria mixture may be provided in either a concentrated form, which will need to be diluted prior to being used, or in a ready to use form, which may be directly applied to the moldable thermoplastic mixture at the appropriate stage in the manufacturing process.

The preferred dry powder carrier is calcium carbonate or sodium bicarbonate in a fine powder form. It has been found that the dry powder form of the benign dormant bacteria mixture does not require a preservative, since the lack of moisture both inhibits germination of the benign dormant bacteria, and inhibits growth of outside bacteria. Thus, the preferred dry powder form of the benign dormant bacteria mixture includes:

0.0001% to 2% w/w of the benign dormant bacteria in a spray dried, powder form; and the remainder being calcium carbonate, or sodium bicarbonate in a fine powder form.

PREPARATION EXAMPLE

A test specimen of product 10 was prepared according to an embodiment of the present invention, as follows.

1. Add 4,086 g (25.58% w/w) of ethylene-vinyl acetate (EVA) resin, g (28.42% w/w) of $CaCO_3$, 908 g (5.68% w/w) of natural rubber, 100 g (0.63% w/w) of zinc oxide (ZnO), 35 g (0.22% w/w) of zinc salt of acid (ZnSt), 1,135 g (7.10% w/w) of polyethylene (PE), and 2,951 g (18.47% w/w) of polyolefin elasotomer (POE) to a mixing machine set to a temperature of between 115° C. and 120° C. Mix the mixture for 5 minutes.

2. Add 120 g (0.75% w/w) of dicumyl peroxide (DCP) cross-linking agent, 450 g (2.82% w/w) of AC foaming/blowing agent, and 1,500 g (9.39% w/w) black color dye to the mixture. Continue mixing for another 5 minutes.

3. Transfer the mixture to a double-roller blending/kneading machine with 21 inch diameter rollers set to a temperature of 110° C. Knead the mixture for about 2 minutes.
4. Add 150 g (0.94% w/w) of an aqueous dormant bacteria mixture comprising about $2.12 \times 10^9$ cfu/ml of *Bacillus megaterium*, *Bacillus subtilus*, and *Licheniformis* in a ratio of about 1:3:6 obtained from Envera LLC, West Chester, Pa., U.S.A, by slowly pouring onto the mixture as it is being blended/kneaded on the roller of the double-roller blending/kneading machine.
5. Knead the mixture for 3 to 6 minutes.
6. Transfer the mixture to a cutting machine to cut the mixture into thin sheets of 1.2 mm thickness.
7. Put stacks of thin sheets about 16 mm high into a mold measuring 150 cm×75 cm×1.6 cm. Insert the mold into a blowing machine set at 171° C. and apply a pressure of 183 kg/cm² for 22 minutes.
8. Release the pressure and remove the blown EVA slabs, which become about 32 mm thick, from the blowing machine.
9. Set the blown EVA slabs aside for a minimum of 2 hours to allow them to cool and shrink to a stable size, resulting in smooth EVA sheets no fine details. The actual time the EVA slabs are to be set aside for will depend on the size and thickness of the EVA slabs, and the temperature and humidity.
10. Cut the EVA sheets into smaller sizes.
11. Trim off the smooth surface of the EVA sheets and cut the EVA sheets to the desired thickness.

The presence of activatable benign dormant bacteria on the surface of the test specimens of the product 10 was tested as follows:
1. Prepare petri dishes containing agar by dispense sterilized tryptic soy broth agar (cooled to 47° C.±2° C.) by pouring 15±2 ml into each standard (15×100 mm) flat bottomed petri dish. Allow the agar to gel firmly.
2. Cut test specimens (non-sterile) of the product 10 by hand using sterile scissors, or with a sterile die, into approximately 1 inch×1 inch squares.
3. For each test specimen press the test specimen into a petri dish to ensure intimate contact of the test specimens with the agar surface.
4. Incubate the petri dishes containing the test specimens for 24 hours at 35° C.
5. Remove the petri dishes containing the test specimens from the incubator.
6. Visually inspect each petri dish to determine the presence or absence of bacterial growth from each test specimen.

Figure 2:
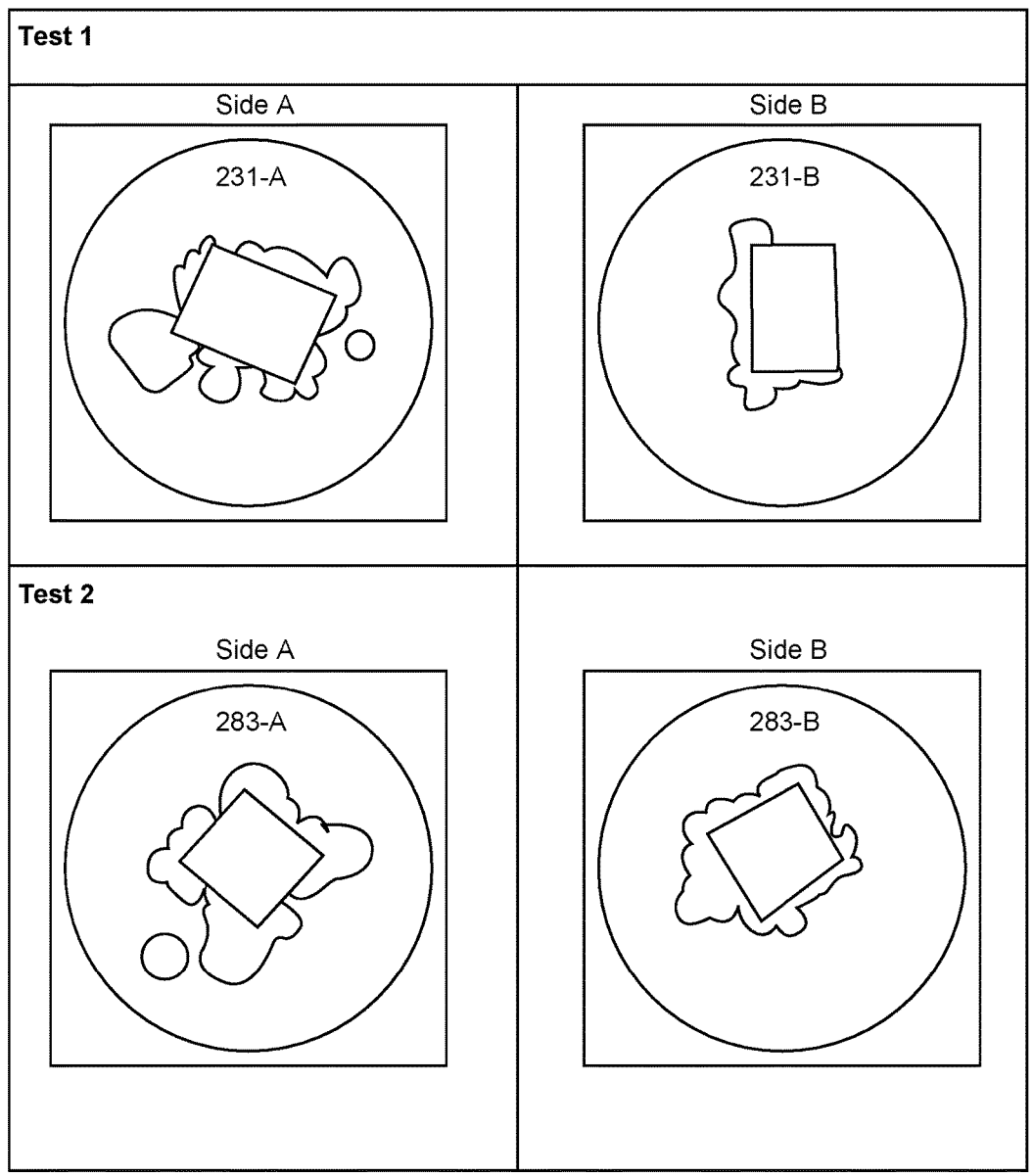

FIG. 2 shows representative test results for two test specimens. The test results show good growth the bacteria in the petri dishes radiating outwardly from the test specimens, confirming that the benign dormant bacteria were present on the surface of the test specimens and activatable upon exposure to organic matter.

The surface population of the benign dormant bacteria in the test specimens of the product 10 was estimated as follows:
1. Prepare 500 ml of tryptic soy broth (TSB) per label directions.
2. Add the 500 ml of TSB to a clean 1-liter baffle flask.
3. Add a stopper and foil covering to the 1-liter baffle flask.
4. Repeat steps 1 to 3 to prepare a second 1-liter baffle flask.
5. Autoclave the 1-liter baffle flasks containing the 500 ml of TSB for 15 minutes at 121° C. and 15 psi.
6. Autoclave a 12"×18" paper wrapped stainless steel plate.
7. Allow the stainless steel plate to cool completely.
8. Cool the 1-liter baffle flasks containing TSB to 80° C. in an 80° C. water bath.
9. Unwrap the stainless steel plate, and place the plate into a biosafety hood.
10. Place a test specimen on top of the stainless steel plate, so that it is laid out flat on the surface of the stainless steel plate.
11. Using a new, disposable scalpel blade attached to a reusable scalpel handle, cut two one-inch squares from the center of the test specimen.
12. Place each one-inch square into one of the sterile 1-liter baffle flasks containing the 500 ml of TSB.
13. Keep the 1-liter baffle flasks in the water bath for 10 minutes.
14. Remove the 1-liter baffle flasks from the water bath and cool to 30° C. in a temperature controlled shaker set at 150 RPM.
15. When the 1-liter baffle flasks have cooled to 30° C., begin timing a 24 hour growth period.
16. At the end of the 24-hour growth period, aseptically transfer 10 ml of the TSB broth from each 1-liter baffle flask to a 90 ml buffer dilution blank.
17. Continue making serial dilutions by adding 10 ml to 90 ml blanks through to a $10^{-6}$ dilution.
18. Plate the $10^4$ through the $10^{-6}$ dilutions onto tryptic soy agar plates.
19. Incubate the tryptic soy agar plates for 24 hours at 35° C.
20. Count the bacterial colonies on each plate.
21. Determine *Bacillus* colony forming units (cfu) per ml from the serial plate count calculations.
22. Divide the serial plate count calculation by 2, to obtain the cfu/ml which is the potential for growth from each one-square inch of the test material.

The results ranged between $1.11 \times 10^9$ and $1.55 \times 10^9$ potential colony forming units of growth per one square inch of test specimen. This test confirmed that the desired number of benign dormant bacteria was exposed on the surfaces of the test specimens of the product 10.

When the surfaces of the test specimens were roughed up by scraping with a piece of plastic, the results ranged between $0.92 \times 10^9$ and $1.33 \times 10^9$ potential colony forming units of growth per one square inch of test specimens. This test confirmed that abrasive wear of the surface of the product 10 exposed sufficient fresh benign dormant bacteria buried in the body to the surface for additional odour control.

The present invention is further described by means of the examples, presented below. The use of such examples is illustrative only and in no way limits the scope and meaning of the invention or of any exemplified term, nor to any particular preferred embodiments described herein. Indeed, many modifications and variations of the invention will be apparent to those skilled in the art upon reading this specification. The invention is therefore to be limited only by the terms of the appended claims.

Figure 3:
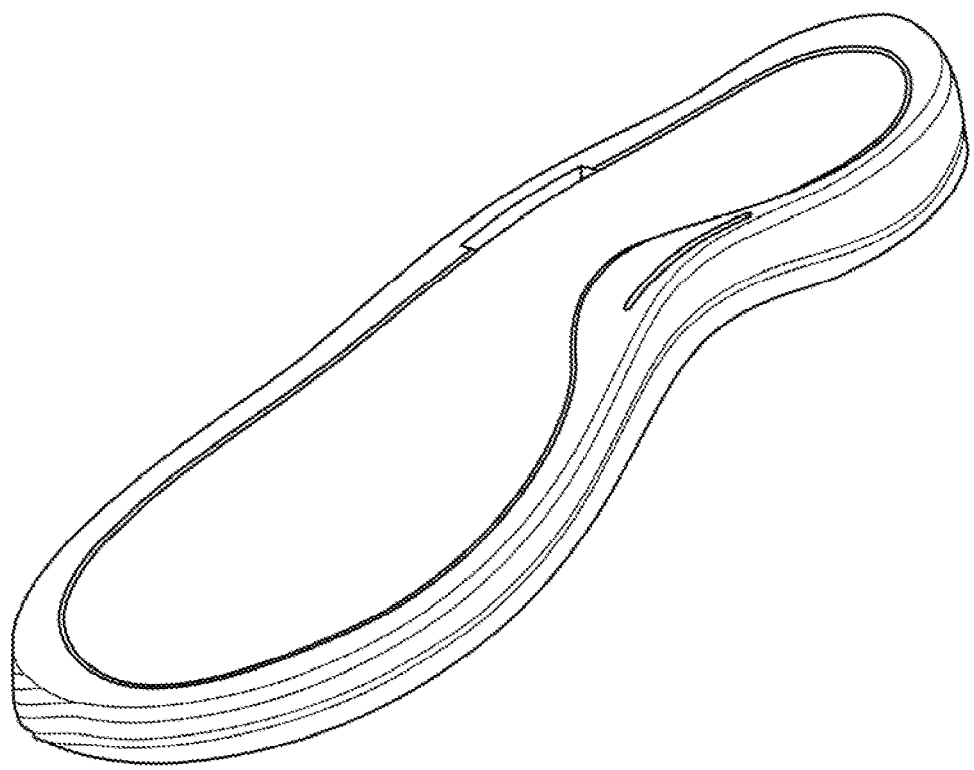

Example 1: Pressed EVA Footbed for Sandal with Benign Dormant Bacteria Embedded Generally Throughout The following example describes a method for making a pressed footbed for a sandal, as shown in FIG. 3. In this example, a sample of an aqueous dormant bacteria mixture was added to EVA and melt-blended as follows.

| INGREDIENTS | Grams | WEIGHT % w/w | SUPPLIER |
|---|---|---|---|
| aqueous dormant bacteria mixture (containing about 2.12 × 10⁹ cfu/ml of *Bacillus megaterium*, *Bacillus subtilus*, and *Licheniformis* in a ratio of about 1:3:6) | 150 | 0.94 | Envera LLC, West Chester, Pennsylvania |
| EVA resin | 4,086 | 25.58 | The Polyolefin Company (Singapore) Pte. Ltd, Singapore; Formosa Plastics Corporation, Taiwan; Braskem, Brazil; Asia Polymer Corporation, Taiwan |
| CaCO₃ (filler) | 4,540 | 28.42 | Shangdong Bo-Liao, China |
| dicumyl peroxide (DCP) cross-linking agent | 120 | 0.75 | Akzo Nobel Cross-linking Peroxides (Ningbo) CO., Ltd., China; Sinopec, China |
| AC foaming/blowing agent | 450 | 2.82 | |
| zinc oxide (ZnO) blowing agent promoter | 100 | 0.63 | Shijiazhuang Zinc Industry Co., Ltd., China; Taiyang, China; Shijiazhuang Zinc Industry Co., Ltd., China |
| zinc salt of stearic acid (ZnSt) blowing agent promoter | 35 | 0.22 | Pt. Sumi Asih Oleochemicals Industry, Indonesia |
| Polyethylene (PE) | 1,135 | 7.10 | National Petrochemical Company, Thailand; PTT Polyethylene Company Limited, Thailand; Kunlun, China |
| Polyolefin Elastomer (POE) | 2,951 | 18.47 | LG Chem, Korea |
| natural rubber | 908 | 5.68 | |
| color dye - black | 1,500 | 9.39 | |
| Total | 15,975 g | 100% | |

Preparing/Mixing EVA Mixture
1. Add the EVA resin, the CaCO₃, the natural rubber, the ZnO, the ZnSt, the PE, and the POE to a mixing machine set to a temperature of between 115° C. and 120° C. Mix the mixture for 5 minutes.
2. Add the dicumyl peroxide (DCP) cross-linking agent, the AC foaming/blowing agent, and the color dye to the mixing machine. Continue mixing the mixture for another 5 minutes.
3. Transfer the mixture to a double-roller blending/kneading machine with 21 inch diameter rollers set to a temperature of 110° C. Knead the mixture for about 2 minutes.
4. Add the aqueous dormant bacteria mixture by slowly pouring it onto the mixture kneading on the roller.
5. Knead the mixture for 3 to 6 minutes.
6. Transfer the mixture to a cutting machine to cut the mixture into thin sheets which are 1.2 mm thick.

Foaming/Blowing
7. Put stacks of the thin sheets about 16 mm high into a mold of 150 cm 75 cm×1.6 cm. Insert the mold into a blowing machine at 171° C. and apply a pressure of 183 kg/cm² for 22 minutes.
8. Release the pressure and remove the blown EVA slabs, which become about 32 mm thick, from the blowing machine.
9. Set the blown EVA slabs aside for a minimum of 2 hours to allow them to cool and shrink to a stable size, resulting in smooth EVA sheets with no fine details. The actual time the EVA slabs are to be set aside for will depend on the size and thickness of the EVA slabs, and the ambient temperature and humidity.

Figure 4:
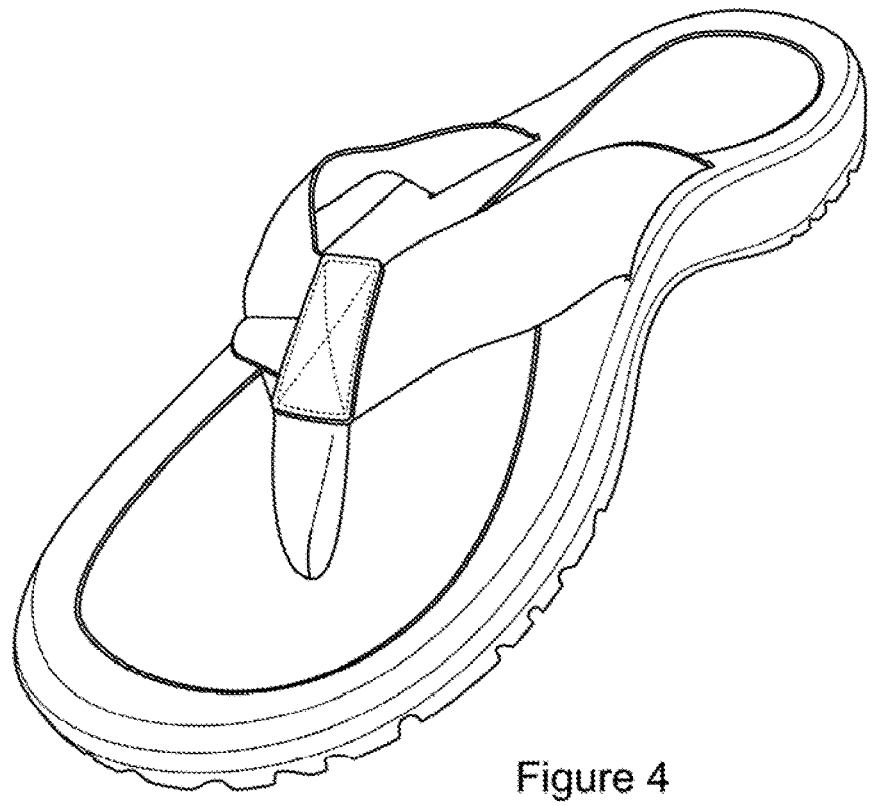

Cutting
10. Cut the EVA sheets to smaller sizes.
11. Trim off the smooth surface of the EVA sheets and cut the EVA sheets to the desired thickness.
12. Cut the EVA sheets through a roller with emboss for a design, resulting in a final, detailed sandal footbed, which is then ready for assembly into a sandal, as shown in FIG. 4.

Example 2: EVA Footbed for Sandal with Benign Dormant Bacteria Embedded Generally Throughout The following example describes a method for making an EVA footbed for a sandal, as shown in FIG. 5. The EVA footbeds according to this embodiment provide two layers: a top layer EVA, which the wearer's foot touches, contains dormant bacteria, and a bottom layer that has no dormant bacteria. In this example, a sample of an aqueous dormant bacteria mixture was added to EVA and melt-blended as follows.

| INGREDIENTS | grams | WEIGHT % w/w | SUPPLIER |
|---|---|---|---|
| aqueous dormant bacteria mixture (containing about 2.12 × 10⁹ cfu/ml of *Bacillus megaterium*, *Bacillus subtilus*, and *Licheniformis* in a ratio of about 1:3:6) | 90 | 0.99 | Envera LLC, West Chester, Pennsylvania |
| EVA resin | 6,300 | 69.31 | The Polyolefin Company (Singapore) Pte. Ltd, Singapore; Formosa Plastics Corporation, Taiwan; Braskem, Brazil; Asia Polymer Corporation, Taiwan |
| CaCO₃ (filler) | 1,440 | 15.84 | Shangdong Bo-Liao, China |
| dicumyl peroxide (DCP) cross-linking agent | 45 | 0.50 | Akzo Nobel Cross-linking Peroxides (Ningbo) CO., Ltd., China; Sinopec, China |
| AC foaming/blowing agent | 135 | 1.49 | |
| Zinc Oxide (ZnO) blowing agent promoter | 90 | 0.99 | Shijiazhuang Zinc Industry Co., Ltd., China; Taiyang, China; Shijiazhuang Zinc Industry Co., Ltd., China |
| Zinc Salt of Stearic Acid (ZnSt) blowing agent promoter | 45 | 0.50 | Pt. Sumi Asih Oleochemicals Industry, Indonesia |
| flow promoting agent | 450 | 4.95 | |
| color dye - black | 495 | 5.45 | |
| Total | 9,090 g | 100% | |

Preparing/Mixing EVA Mixture
1. Add the aqueous dormant bacteria mixture to the CaCO₃ filler.
2. Add the EVA resin, the CaCO₃ and dormant bacteria mixture, the ZnO, the ZnSt, and the color dye to a blending/kneading machine set to an initial temperature of 90° C. and gradually rising at a rate of about 1.5° C./min. Knead for about 6 minutes.

3. Add the dicumyl peroxide (DCP) cross-linking agent, the AC-foaming agent, and the flow promoting agent to the blending/kneading machine and continue kneading for another 6 minutes, with the temperature of the blending/kneading machine continuing to gradually rise at a rate of 1.5° C./min to 108° C.

4. Transfer the mixture to a pellet-making machine set to a temperature of 90° C., in which the material is cut to round EVA flat pellets measuring 4 mm in diameter and 1-3 mm thick.

Initial Foaming/Molding to rough EVA Footbed

5. Put the pellets into molds for foaming at 165° C., pressed at 150 kg/cm² for 15 minutes for Men's and 13 minutes for Women's, according to the following weights:
   a. for men's size 10, total 140 g:
      top layer—87 g EVA pellets with benign dormant bacteria
      bottom layer—53 g EVA pellets without benign dormant Bacteria
   b. for women's size 8, total 99 g:
      top layer—68 g EVA pellets with benign dormant bacteria
      bottom layer—31 g EVA pellets without benign dormant bacteria 6. Remove the rough EVA footbeds from the molds and allow them to cool. The rough EVA footbeds are smooth, slightly larger, general shaped footbeds, with no fine details.

7. Buff the surfaces of the rough EVA footbeds.

Final Shaping

8. Mold the rough EVA footbeds at a hot pressing temperature of 165° C. and a pressing pressure of 80 kg/cm² for 390 seconds for men's and 360 seconds for women's.

9. Cold shape the footbeds at 40° C. for 460 seconds.

10. Trim the final, detailed footbeds, which are then ready for assembly into sandals, an example of which is shown in FIG. 6.

Example 3: EVA Footbed for Sandal with Benign Dormant Bacteria Embedded Generally Throughout The following example describes an alternate method for making an EVA footbed for a sandal, as shown in FIG. 5. In this example, a sample of an aqueous dormant bacteria mixture was added to EVA and melt-blended as follows.

| INGREDIENTS | WEIGHT | | SUPPLIER |
|---|---|---|---|
| | grams | % w/w | |
| aqueous dormant bacteria mixture (containing about 2.12 × 10⁹ cfu/ml of *Bacillus megaterium*, *Bacillus subtilus*, and *Licheniformis* in a ratio of about 1:3:6) | 33 | 1.01 | Envera LLC, West Chester, Pennsylvania |
| EVA resin | 2,280 | 69.47 | The Polyolefin Company (Singapore) Pte. Ltd, Singapore; Formosa Plastics Corporation, Taiwan; Braskem, Brazil; Asia Polymer Corporation, Taiwan |
| CaCO₃ (filler) | 600 | 18.28 | Shangdong Bo-Liao, China |
| dicumyl peroxide (DCP) cross-linking agent | 15 | 0.46 | Akzo Nobel Cross-linking Peroxides (Ningbo) CO., Ltd., China; Sinopec, China |
| AC foaming/blowing agent | 84 | 2.56 | |
| Zinc Oxide (ZnO) blowing agent promoter | 30 | 0.91 | Shijiazhuang Zinc Industry Co., Ltd., China; Taiyang, China; Shijiazhuang Zinc Industry Co., Ltd., China |
| Zinc Salt of Stearic Acid (ZnSt) blowing agent promoter | 15 | 0.46 | Pt. Sumi Asih Oleochemicals Industry, Indonesia |
| flow promoting agent | 18 | 0.55 | |
| color dye - black | 180 | 5.48 | |
| plasticizer | 27 | 0.82 | |
| Total | 3,249 g | 100% | |

Preparing/Mixing EVA Mixture

1. Add the EVA resin, the CaCO₃, the ZnO, and the ZnSt into a mixer set to a temperature of between 105° C. and 110° C.

2. Mix the mixture for about 12 minutes.

3. Remove the mixture from the mixer and roll it into 40 cm×60 cm×2 mm slabs.

4. Transfer 2,925 g of the slabs to a double-roller blending/kneading machine with 40 cm diameter rollers set to a temperature of 90° C. Knead for about 2 minutes.

5. Add the aqueous dormant bacteria mixture to the blending/kneading machine. Knead for 2 minutes.

6. Add the flow promoting agent, the color dye-black, and the plasticizer (preferably at the same time by pouring out of a pre-mixed bag). Knead for 2 minutes.

7. Add the dicumyl peroxide (DCP) cross-linking agent, and the AC foaming/blowing agent (preferably at the same time by pouring out of a pre-mixed bag). Knead for 6 minutes.

8. Remove the mixture from the blending/kneading machine and roll it out into one big flat sheet about 3 mm thick. Set aside the sheet and allow it to cool down.

9. Cut the sheet into small pellets measuring 3 mm×6 mm×9 mm.

Initial Foaming/Molding to rough EVA Footbed

10. Put the pellets into molds for foaming at 160° C., pressed at 180-200 kg/cm² for 680 seconds, according to the following weights:
   a. for men's size 10: 98.5 g
   b. for women's size 8: 80 g.

11. Remove the rough EVA footbeds from the molds and allow them to cool. The rough EVA footbeds are smooth, slightly larger, general shaped footbeds, with no fine details.

12. Buff the surfaces of the rough EVA footbeds.

Final Shaping

13. Mold the rough EVA footbeds at a hot pressing temperature of 150° C. and a pressing pressure of 55 kg/cm² for 460 seconds.

14. Cold shape the foot beds at 40° C. for 460 seconds.
15. Trim the final, detailed footbeds, which are then ready for assembly into a sandal, an example of which is shown in FIG. 6.

Example 4: EVA Insole with Benign Dormant Bacteria Embedded Generally Throughout The following example describes a method for making an EVA insole for a shoe, as shown in FIG. 7. In this example, an aqueous dormant bacteria mixture was added to EVA and melt-blended as follows.

| INGREDIENTS | WEIGHT grams | % w/w |
|---|---|---|
| aqueous dormant bacteria mixture (containing about 2.12 × 10⁹ cfu/ml of *Bacillus megaterium*, *Bacillus subtilus*, and *Licheniformis* in a ratio of about 1:3:6) obtained from Envera LLC, West Chester, Pennsylvania | 28 | 0.99 |
| EVA resin | 1,000 | 35.38 |
| dicumyl peroxide (DCP) cross-linking agent | 51.18 | 1.81 |
| AC foaming/blowing agent | 110.27 | 3.90 |
| zinc oxide (ZnO) blowing agent promoter | 50 | 1.77 |
| zinc salt of stearic acid (ZnSt) blowing agent promoter | 25 | 0.88 |
| polyethylene (PE) or polyolefin elastomer (POE) | 1,500 | 53.08 |
| color dye - black | 41.61 | 1.47 |
| powder (Tyressen Co., Ltd., 426-19 Yeocheon Dong, Nam-gu, Ulsan, South Korea) | 20.06 | 0.71 |
| Total | 2,826.12 g | 100% |

Preparing/Mixing EVA Mixture
1. Mix the ZnO and ZnSt powders in a container and add the aqueous dormant bacteria mixture.
2. Add the EVA resin, and the PE or POE into a mixer set to a temperature of 80° C., and a mixing speed of 500 to 580 rpm.
3. Mix the mixture for about 1 minute.
4. Add the mixture of ZnO, ZnSt, and dormant bacteria mixture from step 1 above to the mixer. Mix the mixture at 90° C. and a mixing speed of 580 to 740 rpm, for 10 minutes.

Kneading
5. Transfer the mixture from step 4 to a double-roller blending/kneading machine with 21 inch diameter rollers set to a temperature of 100° C. Knead for about 5 minutes.
6. Add the AC foaming agent and the color dye to the mixture. Continue mixing the mixture for another 3.5 minutes.
7. Add the dicumyl peroxide (DCP) cross-linking agent, and the powder to the mixture. Continue mixing the mixture for another 5 minutes.

Blowing/Foaming
8. Transfer a portion of the mixture from step 7 into a mold measuring 17.5 cm×12 cm×2.3 cm.
9. Insert the mold into a blowing machine at 160° C. and apply a pressure of 155 kg/cm² for 35 minutes.
10. Release the pressure and take the blown EVA slab from the mold.
11. Set the blown EVA slab aside to cool and shrink to its stable size. Results in a smooth EVA sheet, with no fine details.
12. Repeat steps 8-11 above until the entire mixture is foamed.

Cutting
13. Cut the EVA sheets into smaller sizes.
14. Trim off the smooth surface of the EVA sheets and cut the EVA sheets to the desired thickness.
15. Cut insoles out from the EVA sheets.

While reference has been made to various preferred embodiments of the invention other variations, implementations, modifications, alterations and embodiments are comprehended by the broad scope of the appended claims. Some of these have been discussed in detail in this specification and others will be apparent to those skilled in the art. Those of ordinary skill in the art having access to the teachings herein will recognize these additional variations, implementations, modifications, alterations and embodiments, all of which are within the scope of the present invention, which invention is limited only by the appended claims.

We claim:

1. A footwear product adapted to control odors arising from organic matter external to said footwear product, said footwear product comprising:
    a self-supporting foam body sized and shaped to support a person's foot, and defining a foot contacting surface;
    said self-supporting foam body comprising an ethylene vinyl acetate (EVA) thermoplastic and sporulated benign dormant bacteria, said self-supporting foam body being formed by melt-blending said EVA thermoplastic and said sporulated benign dormant bacteria together, and molding said melt-blend to form said self-supporting foam body;
    said sporulated benign dormant bacteria being embedded throughout said self-supporting foam body, including being buried within said self-supporting foam body and being directly exposed on said foot contacting surface;
    said sporulated benign dormant bacteria directly exposed on said foot contacting surface being activatable upon exposure of said foot contacting surface to said external organic matter, wherein said activated benign bacteria digest said external organic matter to control production of offensive odors, without digesting said self-supporting foam body; and
    said self-supporting foam body being adapted to allow abrasive wear of said foot contacting surface by said person's foot during use of said footwear product to expose fresh sporulated benign dormant bacteria, buried within said self-supporting foam body on said foot contacting surface for additional odor control.

2. The footwear product according to claim 1, wherein at least $10^6$ of said sporulated benign dormant bacteria are present per square inch of said foot contacting surface.

3. The footwear product according to claim 1, wherein at least $10^{12}$ of said sporulated benign dormant bacteria are present per cubic inch of said self-supporting foam body.

4. The footwear product according to claim 2, wherein at least $10^{16}$ of said sporulated benign dormant bacteria are present per cubic inch of said self-supporting foam body.

5. The footwear product according to claim 1, wherein said self-supporting foam body is an open-cell foam.

6. The footwear product according to claim 1, wherein said self-supporting foam body is a closed-cell foam.

7. The footwear product according to claim 1, which is wherein molding comprises compression molding, injection molding, blow molding or extrusion molding.

8. The footwear product according to claim 1, wherein said sporulated benign dormant bacteria comprises at least one strain of the genus *Bacillus*.

9. The footwear product according to claim 8, wherein said *Bacillus*, when activated, produces an enzyme to break down and assist with said digesting of said external organic matter.

10. The footwear product according to claim 9, wherein said *Bacillus* produces water and carbon dioxide as by-products of said break down and digesting of said external organic matter.

11. The footwear product according to claim 9, wherein said *Bacillus* returns back to a sporulated dormant state after said external organic matter has been digested, and is re-activatable upon exposure of said foot contacting surface to additional external organic matter, wherein said re-activated benign bacteria digests said additional external organic matter to control production of offensive odors, without digesting said self-supporting foam body.

12. The footwear product according to claim 9, wherein said *Bacillus* is selected from the group consisting of *Bacillus megaterium, Bacillus subtilis, Bacillus licheniformis, Bacillus cerus, Bacillus alvei, Bacillus coagulans, Bacillus pumillus, Bacillus simplex, Bacillus brevis*, and *Bacillus amyloliquefaciens*.

13. The footwear product according to claim 12, wherein said sporulated dormant bacteria comprises *Bacillus megaterium, Bacillus subtilis*, and *Bacillus licheniformis*.

14. The footwear product according to claim 1, wherein said self-supporting foam body is an insole, or a footbed.

15. A textile product adapted to control offensive odors arising from organic matter external to said textile product, said textile product comprising:
   a fiber sized and shaped to be used in weaving, knitting, or felting, and defining an external surface;
   said fiber comprising an ethylene-vinyl acetate (EVA) thermoplastic and sporulated benign dormant bacteria, said fiber being formed by melt-blending said EVA thermoplastic and said sporulated benign dormant bacteria together, and extruding said melt-blend into said fiber;
   said sporulated benign dormant bacteria being embedded throughout said fiber, including being buried within said fiber and being directly exposed on said external surface;
   said sporulated benign dormant bacteria exposed on said external surface being activatable upon exposure of said external surface to said external organic matter, wherein said activated benign bacteria digest said external organic matter to control production of said offensive odors, without digesting said fiber; and
   said fiber being adapted to allow abrasive wear of said external surface during use of said textile product to expose fresh sporulated benign dormant bacteria, buried within said fiber, on said external surface for additional odor control.

16. The textile product according to claim 15, wherein said fiber is a thread, or a yarn.

17. The textile product according to claim 16, which is bedding, drapery, upholstery, a towel, or an article of clothing.

18. The textile product according to claim 16, which is a floor covering, a carpet, a carpet tile, a mat, or a rug.

19. The footwear product according to claim 1, wherein said external organic matter is a bodily fluid or organic waste, and said bodily fluid or organic waste contains sufficient carbon, nitrogen and moisture to activate said sporulated benign dormant bacteria.

20. The footwear product according to claim 19, wherein said bodily fluid is feces, urine, sweat, blood, saliva, or semen.

21. The footwear product according to claim 19, wherein said organic waste is milk, wine, a soft drink, syrup, or an egg.

22. A method of making the footwear product according to claim 1, comprising the steps of:
   a) melt-blending at a bacteria compatible temperature range:
      i) said EVA thermoplastic; and
      ii) said sporulated benign dormant bacteria; and
   b) molding the melt-blended product of step (a) into said footwear product.

23. The method according to claim 22, wherein at least $10^6$ of said sporulated benign dormant bacteria are present per square inch of said foot contacting surface.

24. The method according to claim 22, wherein at least $10^{12}$ of said sporulated benign dormant bacteria are present per cubic inch of said footwear product.

25. The method according to claim 23, wherein at least $10^{16}$ of said sporulated benign dormant bacteria are present per cubic inch of said footwear product.

26. The method according to claim 22, wherein said sporulated benign dormant bacteria comprises an aqueous carrier.

27. The method according to claim 22, wherein said sporulated benign dormant bacteria comprises a dry powder carrier.

28. The method according to claim 27, wherein said dry powder carrier comprises calcium carbonate or sodium bicarbonate.

29. The method according to claim 26, wherein the concentration of said sporulated benign dormant bacteria in said carrier is about 0.0001% to 2% by weight.

30. The method according to claim 27, wherein the concentration of said sporulated benign dormant bacteria in said carrier is about 0.0001% to 2% by weight.

31. The method according to claim 28, wherein the concentration of said sporulated benign dormant bacteria in said carrier is about 0.0001% to 2% by weight.

32. The method according to claim 22, wherein said sporulated benign dormant bacteria comprises at least one strain of the genus *Bacillus*.

33. The method according to claim 32, wherein said *Bacillus* is selected from the group consisting of *Bacillus megaterium, Bacillus subtilis, Bacillus licheniformis, Bacillus cerus, Bacillus alvei, Bacillus coagulans, Bacillus pumillus, Bacillus simplex, Bacillus brevis*, and *Bacillus amyloliquefaciens*.

34. The method according to claim 33, wherein said dormant bacteria comprises *Bacillus megaterium, Bacillus subtilis*, and *Bacillus licheniformis*.

35. The method according to claim 22, wherein said molding step comprises the steps of:
   kneading said melt-blend at a temperature of about 20° C. to about 25° C.;
   rolling said kneaded melt-blended product into a sheet;
   compressing said sheet;
   heating said sheet to about 170° C. to about 175° C., at a pressure of about 150 kg/cm$^2$; and
   compression molding said sheet at about 160° C.

36. The method according to claim 22, wherein said molding step comprises injection molding, blow molding or extrusion molding.

37. The method according to claim 36, further comprising compression molding said injection molded, blow molded, or extrusion molded product.

38. The textile product as according to claim 15, comprising a plurality of said fiber, wherein said plurality of said fibers are woven, knitted, or felted together.

* * * * *

UNITED STATES PATENT AND TRADEMARK OFFICE
CERTIFICATE OF CORRECTION

Page 1 of 2

PATENT NO. : 9,974,311 B2
APPLICATION NO. : 14/034109
DATED : May 22, 2018
INVENTOR(S) : Chow et al.

It is certified that error appears in the above-identified patent and that said Letters Patent is hereby corrected as shown below:

In the Specification

Column 1:
Line 8, "Materials" should read --The invention concerns materials--,
Line 12, "to a" should read --to set up a--,
Line 53, "Sp." should read --*Sp.*--,
Line 56, "Sp." should read --*Sp.*--,
Line 59, "baby" should read --for baby--, and
Line 61, "2-2-121,665" should read --2-121,665--.

Column 2:
Line 29, "3,720,606," (2nd occurrence) should be deleted,
Line 36, "99/46350," should read --97/43385, 99/46350--,
Line 52, "WEST" should read --VIEST--,
Line 60, "Supress" should read --Suppress--, and
Line 61, "Magaterium" should read --*Magaterium*--.

Column 3:
Line 1, "Supress" should read --Suppress--,
Line 28, "mats" should read --mats,--, and
Line 49, "of a" should read --of--.

Column 4:
Line 47, "dormant" should read --dormant bacteria--.

Column 5:
Line 65, "provide" should read --provide that--.

Column 6:
Line 3, "per" should read --per se.--,

Signed and Sealed this
Eleventh Day of September, 2018

Andrei Iancu
*Director of the United States Patent and Trademark Office*

Line 16, "generally," should read --general,--,
Line 41, "molded" should read --molded product,--, and
Line 47, "upon" should read --and upon--.

Column 7:
Line 22, "for" should read --for about--,
          "minutesduring" should read --minutes during--, and
Line 38, "sheets, in" should read --sheets. In--.

Column 8:
Line 45, "present" should read --present invention--.

Column 9:
Line 9, "comprise" should read --be comprised--,
Line 35, "Bacillus, Alvei" should read --Bacillus Alvei--, and
Line 60, "being applied to the kneading moldable" should read --being kneaded in the moldable--.

Column 10:
Line 57, "resin, g" should read --resin, 4,540 g--,
Line 59, "acid" should read --stearic acid--, and
Line 61, "elasotomer" should read --elastomer--.

Column 11:
Line 24, "no" should read --with no--,
Line 34, "dispense" should read --dispensing--, and
Line 51, "growth" should read --growth for--.

Column 12:
Line 26, "$10^4$" should read --$10^{-4}$--, and
Line 65, "pressed" should read --pressed EVA--.

Column 13:
Line 62, "150 cm 75 cm×1.6cm." should read --150 cm×75 cm×1.6cm.--.

Column 15:
Line 22, "Bacteria" should read --bacteria--.

In the Claims

Column 18:
Line 47, "body" should read --body,--, and
Line 62, "which is" should be deleted.

Column 21:
Line 4, "as" should be deleted.